United States Patent [19]

Delahaye et al.

[11] Patent Number: 5,357,043
[45] Date of Patent: Oct. 18, 1994

[54] PREPARATION OF OLIGOPEPTIDE OR AMINO ACID ALKYL ESTER.HCL SALTS

[75] Inventors: Hubertus J. A. V. Delahaye, Nuth; Johan T. Tinge, Sittard; Adelbert A. H. Drinkenburg; Antonius J. J. M. Teunissen, both of Geleen; Willem Klop, Limbricht, all of Netherlands

[73] Assignee: Holland Sweetener Company V.O.V., Maastricht, Netherlands

[21] Appl. No.: 993,008

[22] Filed: Dec. 18, 1992

[30] Foreign Application Priority Data

Dec. 20, 1991 [NL] Netherlands ............... 9102143

[51] Int. Cl.$^5$ ............... C07K 3/04; C07K 3/08
[52] U.S. Cl. ............... 530/334; 530/333; 530/335; 530/345
[58] Field of Search ............... 530/334, 333, 335, 345

[56] References Cited

U.S. PATENT DOCUMENTS 4,173,562 11/1979 Bachman et al.
4,709,013 11/1987 Nagano ............... 530/332
4,784,685 11/1988 Meister ............... 71/106

FOREIGN PATENT DOCUMENTS 0313909 5/1989 European Pat. Off.
1493991 10/1969 Fed. Rep. of Germany
286188 5/1964 Netherlands

OTHER PUBLICATIONS

Chemical Abstracts, vol. 109, No. 19, Nov. 7, 1988, Abstract No. 170936w (JP-A-63 159 363).

Primary Examiner—Merrell C. Cashion, Jr.
Assistant Examiner—Carol Salata
Attorney, Agent, or Firm—Cushman, Darby & Cushman

[57] ABSTRACT

The invention relates to a process for the preparation of an oligopeptide or amino acid alkyl ester.HCl salt, the alkyl group being methyl, ethyl, isopropyl or n-propyl, by converting an oligopeptide.HCl salt or amino acid.HCl salt with an alkanol corresponding to the alkyl group under the influence of an acid catalyst, 0.01–0.5 mol HCl relative to the oligopeptide.HCl salt or amino acid.HCl salt in combination with an acid ion exchange resin being used as acid catalyst.

16 Claims, No Drawings

PREPARATION OF OLIGOPEPTIDE OR AMINO ACID ALKYL ESTER.HCL SALTS

The invention relates to a process for the preparation of an oligopeptide or amino acid alkyl ester.HCl salt, the alkyl group being methyl, ethyl, isopropyl or n-propyl, by converting an oligopeptide.HCl salt or amino acid.HCl salt with an alkanol corresponding to the alkyl group under the influence of an acid catalyst.

Such an esterification process is known for amino acids (Beilstein's Organic Chemistry Manual, 4th edition (1985), volume 14, part 3, pp. 1555–1556).

In the preparation of the esters according to the processes described, the alkanol is saturated with HCl. In such a process 15–20 mol HCl per mol oligopeptide or amino acid is used. In industrial practice the quantity of HCl applied is considerably lower, but it remains necessary to use a relatively large quantity of HCl: about 1 mol relative to the HCl salt. After the esterification this excess of HCl has to be removed, for instance by salt formation with a base or by distillation of HCl with the solvent. A drawback of this process moreover is that relatively much alkylchloride is formed as by-product, which is environmentally harmful. Further, the HCl, which has to be used in (dry) gaseous form, is relatively costly.

According to EP-A-313909 the propyl ester of phenylalanine can be prepared with a good yield with application of a smaller quantity of HCl as acid catalyst if the water formed during the reaction is immediately removed by means of azeotropic distillation. However, a drawback attaching to azeotropic distillation is that a (azeotropic) solvent has to be added, which means adding a potential impurity. Moreover, if methanol is used as alkanol for preparation of an oligopeptide or amino acid methyl ester, an azeotrope is not well possible.

The objective of the invention is a process for the preparation of oligopeptide or amino acid alkyl ester.HCl salts, in which the alkyl group may be methyl, ethyl, isopropyl or n-propyl, in which only little alkylchloride is formed and in which it is possible to apply a significantly smaller quantity of HCl than a molar excess.

This objective is accomplished according to the invention by using as acid catalyst 0.01–0.5 mol HCl relative to the oligopeptide.HCl salt or amino acid.HCl salt in combination with an acid ion exchange resin in the process for the preparation of an oligopeptide or amino acid alkyl ester.HCl salt, in which the alkyl group is methyl, ethyl, isopropyl or n-propyl and in which an oligopeptide.HCl salt or amino acid.HCl salt is converted with an alkanol corresponding to the alkyl group under the influence of an acid catalyst.

It is unexpected that with a relatively small amount of HCl in combination with an acid ion exchange resin a good conversion is achieved, with virtually no formation of alkylchloride any more.

In itself, the application of an acid ion exchange resin for esterification reactions is described in WO-A-90/08127. However, in that case it is concerned with alkyl carboxylic acids which do not contain alkaline amino groups. Moreover, no extra acid is used. Further, it is also known from Houben-Weyl (1974, volume XV/I, p. 320) to use an acid ion exchange resin as catalyst for the esterification of the carboxyl group of amino acids. In that process, no HCl salt is used and neither is extra acid used, and the yield values are low (~70%). It appears that without the presence of HCl the use of an acid ion exchange resin does not result in a good yield. The addition of HCl moreover offers the advantage of raising the reaction rate.

Since an esterification reaction is an equilibrium reaction, it is advantageous to apply an excess quantity of the alkanol with which the oligopeptide or amino acid.HCl salt has to be esterified. The alkanol can as a rule be use as solvent and is preferably present in such a quantity that the ratio to the amino acid is (5–25):1, in particular (10–20):1.

The process is carried out in the liquid phase, as a rule at a temperature between 25° and 105° C., preferably 40°–100° C., in particular 50°–80° C., and a pressure of between 0.1 and 10 bar, preferably between 0.5 and 2.0 bar, in particular at about atmospheric pressure.

Preferably, 0.05–0.4 mol HCl relative to the oligopeptide or amino acid.HCl salt is applied because then a high yield is obtained, while only very little alkylchloride is formed.

Any strongly acid ion exchange resin can be used as ion exchange resin. Very suitable ion exchange resins are sulphonated polystyrene divinylbenzene resins. Useful ion exchange resins are e.g. strongly acid ion exchange resins as described in Ullman (1989) A14, pp. 393–405 and p. 451. The ion exchange resins are used in protonated form. Suitable ion exchange resins of this category are e.g. Dowex ® (from DOW Chemical), Lewatit ® SP 120 (from Bayer) or Amberlyst ® (from Rohm & Haas). The exchange resins as a rule have 3–6, preferably 4–5 meq acid groups per gramme of dry ion exchange resin.

A strongly acid ion exchange resin in the H+ form is deactivated by metal ions such as for instance Na+ and $Ca^{2+}$. The applicant has found that such deactivation can be counteracted by using more HCl, but it is preferable to keep the concentration of metal ions low, preferably below 50 mM, in particular below 20 mM. Polyvalent metal ions affect the activity of the ion exchange resin to a stronger extent; therefore it is preferable to keep the concentration below 10 mM.

The reaction can advantageously be carried out by preparing a reaction mixture comprising the alkanol, the oligopeptide or amino acid.HCl salt and 0.01–0.5 mol HCl. If desired, the esterification reaction may already be partially effected in this reaction mixture (in the absence of the ion exchange resin) for 0.1–10 h at 25°–105° C. The reaction mixture—if desired after partial esterification—is preferably led through a column containing the ion exchange resin, at a velocity (LHSV: liquid hourly space velocity) of for instance 0.05–1 liter of reaction mixture per liter of ion exchange resin per hour. Preferably, so much ion exchange resin is applied that the reaction mixture is in contact with the ion exchange resin for 0.3–10 h.

The process according to the invention can be used to carry out esterification reactions with realization of yields of more than 80%, even more than 90%, in spite of the presence of any small quantities of metal ions and the presence of 1–2% water.

The process can be applied to all amino acid.HCl salts, in particular those of the natural amino acids, non-natural optical isomers thereof and (racemic) mixtures of both. In particular, the process is suitable for the esterification of the carboxyl group in phenylalanine (Phe). The methyl ester of Phe is an important starting material in the manufacture of aspartame (L-α-aspartyl-L-phenylalanine methyl ester).

Further, the process can very suitably be applied to oligopeptide.HCl salts. By oligopeptides in the present application are meant peptides comprised of 2–9 amino acids. The amino acids are as mentioned above.

In the application of the invention it has also appeared that amino acids (or oligopeptides) having an extra free carboxyl group in the side chain can be esterified as well. By adaptation of the reaction time, the reaction temperature and the degree of dilution, and addition of water the reaction can be so controlled in that case that completer conversion to di-ester is achieved, or more of the ester is linked to one of the carboxyl groups. As dipeptide can be used for instance L-α-aspartyl-L-phenylalanine (AP). In the pharmaceutical industry oligopeptides of for instance 5 or 6 amino acids are used. In so far as those pharmaceutical products have one or more ester groups with 1–3 carbon atoms, they can be produced most advantageously by the process according to the present invention.

The product obtained by the process according to the invention can directly be used further, whether or not after neutralization, as a solution; also, the oligopeptide or amino acid alkyl ester.HCl salt can be recovered for instance by distilling off the alkanol and the excess of HCl. Also, the excess of HCl can be neutralized, after which the HCl salt can be separated and/or purified by e.g. extraction, crystallization or other methods known to one skilled in the art. If the oligopeptide alkyl ester or amino acid alkyl ester is the desired product, it can be recovered by neutralizing the HCl salt and recovering the alkyl ester in a known manner.

The invention will now be elucidated with reference to the following non-restrictive examples.

EXAMPLE I 1 mol DL-Phe, 15 mol methanol and 1.1 mol HCl were introduced into a reaction vessel. 300 ml ion exchange resin (Lewatit ® SP 120) was added to this mixture; the reaction mixture obtained was stirred for 3 hours at 60° C.

The quantity of methylchloride formed amounted to 0.03 mol per mol DL-Phe methyl ester (this is ~5×less than when 1.9 mol HCl and no ion exchange resin were used) and the yield of DL-Phe methyl ester.HCl salt was 88%.

EXAMPLE II

A continuous esterification experiment was carried out in a double-walled glass column (diameter 3.4 cm, length 23 cm), filled with 210 ml Lewatit ® SP 120 ion exchange resin in H+ form. 29 wt. % DL-Phe.HCl in methanol and 0.05 mol HCl (per mol DL-Phe.HCl) were led through the column for 4 days. The reaction mixture that had to be led through the column yet was kept at room temperature during the 4 days. The reaction mixture was led through the column with an LHSV (liquid hourly space velocity) of 0.13 ml/ml ion exchange resin/h at a reaction temperature of 60° C. The degree of conversion was almost constantly 91%. The amount of methylchloride amounted to 0.016 mol/mol DL-Phe methyl ester.HCl.

EXAMPLE III

Analogously to example II, a continuous experiment was carried out with a column (diameter 1.5 cm, length 21 cm) with a content of 38 ml. Instead of DL-Phe, L-Phe was used, which solution was stored at 5° C., so that (virtually) no prior reaction took place. The LHSV was 0.25 ml/ml ion exchange resin/h. After 9 days the conversion was still 91%; the amount of methylchloride was 0.017 mol per mol L-Phe methyl ester.HCl.

EXAMPLE IV

The reaction was carried out analogously to example III, making sure that the L-Phe solution contained 660 mg NaCl per kg solution. Further, a molar HCl/Phe ratio of 1.1 was chosen. The LHSV was 0.26 at a temperature of 65° C.; the conversion amounted to ~85%. The ion exchange resin, after reaching equilibrium conversion, did not show a decline in activity for 2½ weeks.

EXAMPLE V

The reaction was carried out analogously to example IV, but now with a molar HCl/Phe ratio of 1.15. The reaction mixture (330 mg NaCl per kg solution) was first led at 65° C. and at an average residence time of 2 hours through a small vessel (about 45% conversion), and subsequently, analogously to Example III, through an ion exchange resin column. The final conversion was 93% after 16 days of operation, 0.05 mol methyl chloride per mol L-Phe methyl ester.HCl being released.

EXAMPLE VI

Analogously to example V an experiment was carried out using Amberlyst ® 15 from Rohm & Haas as ion exchange resin. Comparable results were obtained.

EXAMPLE VII

Analogously to example VI an experiment was carried out with an HCl/Phe ratio of 1.35 and an LHSV of 0.2. The conversion was 95%.

EXAMPLE VIII

Into a suspension of 50 ml dry Amberlyst ® 15 and 160 g (5 mol) dry methanol, 0.020 mol hydrochloric acid gas was supplied with stirring at 20° C. in 34 sec. Immediately afterwards, 0.249 mol AP.HCl salt (78.8 g) was added in a short time and the temperature was raised to 65° C. The results are shown in the table below:

| Time (min.) | Mol. % AP* conversion | Mol. % selectivity | | |
|---|---|---|---|---|
| | | AP-α-methyl ester** | AP-β-methyl ester | AP-dimethyl ester |
| 15 | 75 | 42 | 19 | 38 |
| 30 | 90 | 38 | 21 | 40 |
| 54 | 94 | 35 | 22 | 41 |
| 108 | 97 | 32 | 22 | 46 |
| 187 | 100 | 27 | 22 | 50 |
| 251 | 100 | 23 | 20 | 56 |

*AP: L-α-aspartyl-L-phenylalanine
**aspartame

We claim:

1. A process for preparing an alkyl ester hydrochloric acid salt of the dipeptide aspartylphenylalanine or an alkyl ester hydrochloric acid salt of the amino acid phenylalanine, wherein said alkyl group can be chosen from the group consisting of methyl, ethyl, isopropyl or n-propyl, which comprises esterifying an aspartylphenylalanine hydrochloric acid salt or a phenylalanine hydrochloric acid salt with a $C_1$–$C_3$ alcohol in the presence of a catalytically effective amount of an acid catalyst, comprising an acid ion exchange resin and hydrochloric acid, wherein said hydrochloric acid is present at a concentration of 0.01–0.5 moles per mole aspartylphenylalanine hydrochloric acid salt or phenylalanine hydrochloric acid salt and wherein said process is carried out in a liquid phase.

2. The process according to claim 1, wherein the aspartylphenylalanine hydrochloric acid salt or the phenylalanine hydrochloric acid salt in combination with the $C_1$–$C_3$ alcohol and hydrochloric acid catalyst are passed through a column containing the ion exchange resin at a rate (liquid hourly space velocity) of 0.05–1 liter reaction mixture per liter ion exchange resin per hour.

3. The process according to claim 1, wherein the ratio of the $C_1$–$C_3$ alcohol to either the aspartylphenylalanine hydrochloric acid salt or the phenylalanine hydrochloric acid salt is 5–25 parts $C_1$–$C_3$ alcohol to 1 part aspartylphenylalanine hydrochloric acid salt or phenylalanine hydrochloric acid salt.

4. The process according to claim 1, wherein the ratio of the $C_1$–$C_3$ alcohol to either the aspartylphenylalanine hydrochloric acid salt or the phenylalanine hydrochloric acid salt is 10–20 parts $C_1$–$C_3$ alcohol to 1 part aspartylphenylalanine hydrochloric acid salt or phenylalanine hydrochloric acid salt.

5. The process according to claim 1, wherein the alcohol is methanol.

6. The process according to claim 1, wherein the esterification is conducted at a temperature of 25°–105° C.

7. The process according to claim 1, wherein the esterification is conducted at a pressure of 0.5–2 bar.

8. The process according to claim 1, wherein the esterification is conducted at about atmospheric pressure.

9. The process according to claim 1, wherein the hydrochloric acid is present at a concentration of 0.05–0.4 moles per mole aspartylphenylalanine hydrochloric acid salt or phenylalanine hydrochloric acid salt.

10. The process according to claim 1, wherein the ion exchange resin is a sulphonated polystyrene-divinylbenzene resin.

11. The process according to claim 1, wherein the esterification is conducted in the presence of the ion exchange resin for 0.3–10 hours.

12. The process according to claim 1, wherein the esterification mixture is maintained at a temperature of 25°–105° C. for 0.1–10 hours prior to continuing the reaction in the presence of the ion exchange resin.

13. A process for preparing an alkyl ester of the amino acid phenylalanine, wherein said alkyl ester hydrochloric acid salt of phenylalanine obtained according to the process of claim 1 is neutralized to form an alkyl ester of phenylalanine and then recovered.

14. A process for preparing an alkyl ester of the dipeptide aspartylphenylalanine, wherein said alkyl ester hydrochloric acid salt of aspartylphenylalanine obtained according to the process of claim 1 is neutralized to form an alkyl ester of aspartylphenylalanine and then recovered.

15. An alkyl ester hydrochloric acid salt of the dipeptide aspartylphenylalanine or an alkyl ester hydrochloric acid salt of the amino acid phenylalanine obtained according to the process of claim 1.

16. The process according to claim 1, wherein the phenylalanine is L-phenylalanine.

* * * * *